United States Patent
Butz et al.

(10) Patent No.: US 9,408,563 B2
(45) Date of Patent: Aug. 9, 2016

(54) PIERCING DEVICE WITH ROTARY ELEMENT

(75) Inventors: Marion Butz, Regensburg (DE); Michael-Martin Strehl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 430 days.

(21) Appl. No.: 14/008,498

(22) PCT Filed: Mar. 15, 2012

(86) PCT No.: PCT/EP2012/054519
§ 371 (c)(1),
(2), (4) Date: Jan. 2, 2014

(87) PCT Pub. No.: WO2012/130619
PCT Pub. Date: Oct. 4, 2012

(65) Prior Publication Data
US 2014/0128897 A1 May 8, 2014

(30) Foreign Application Priority Data

Mar. 31, 2011 (DE) .......................... 10 2011 015 758

(51) Int. Cl.
*A61B 17/14* (2006.01)
*A61B 5/15* (2006.01)
*A61B 5/151* (2006.01)

(52) U.S. Cl.
CPC .............. *A61B 5/1411* (2013.01); *A61B 5/1519* (2013.01); *A61B 5/150022* (2013.01); *A61B 5/15113* (2013.01); *A61B 5/15117* (2013.01); *A61B 5/15128* (2013.01); *A61B 5/150412* (2013.01); *A61B 5/150503* (2013.01); *A61B 5/15003* (2013.01)

(58) Field of Classification Search
CPC ........... A61B 5/1411; A61B 5/150022; A61B 5/15003; A61B 5/150412; A61B 5/15113; A61B 5/15128; A61B 5/1519
See application file for complete search history.

(56) References Cited

U.S. PATENT DOCUMENTS

| 4,924,879 A | 5/1990 | O'Brien |
| 5,545,174 A | 8/1996 | Schenk et al. |

(Continued)

FOREIGN PATENT DOCUMENTS

| EP | 1090584 A2 | 4/2001 |
| WO | WO 2008/107382 A1 | 9/2008 |
| WO | WO 2009/147080 A1 | 12/2009 |

OTHER PUBLICATIONS

International Search Report, International Application No. PCT/EP2012/054519, English Language, Jul. 2, 2012, 3 pages.

(Continued)

*Primary Examiner* — Robert Lynch
(74) *Attorney, Agent, or Firm* — Lathrop & Gage LLP (57) ABSTRACT

The invention relates to a piercing device for taking blood for medical analyses, comprising a base body, comprising at least one needle which is arranged therein and a tip which can be extended, comprising a needle holding element which encloses the needle at least in part and a drive unit for driving a movement of the needle together with the needle holding element with respect to the base body.

11 Claims, 10 Drawing Sheets

(56) References Cited

U.S. PATENT DOCUMENTS

| | | | |
|---|---|---|---|
| 8,827,925 B2* | 9/2014 | Butz | A61B 5/1433 606/182 |
| 8,828,039 B2* | 9/2014 | Butz | A61B 5/1411 606/182 |
| 2005/0131441 A1 | 6/2005 | Iio et al. | |
| 2005/0145520 A1 | 7/2005 | Ilo et al. | |
| 2010/0069943 A1* | 3/2010 | Roe | A61B 5/1411 606/181 |
| 2010/0152759 A1* | 6/2010 | List | A61B 5/1411 606/172 |

OTHER PUBLICATIONS

International Preliminary Report on Patentability, International Application No. PCT/EP2012/054519, English translation, Oct. 2, 2013, 7 pages.

International Preliminary Report on Patentability, International Application No. PCT/EP2012/054519, German, 5 pages.

Office Action dated Nov. 15, 2014, from Chinese Application No. 2012 800167738, 14 pp.

* cited by examiner

PIERCING DEVICE WITH ROTARY ELEMENT

CROSS REFERENCE TO RELATED APPLICATIONS

This application is a U.S. National Stage Application under 35 U.S.C. §371 of International Application No. PCT/EP2012/054519, filed Mar. 15, 2012, which claims the benefit of and priority to German Application No. 10 2011 015 758.1, filed on Mar. 31, 2011, each of which is hereby incorporated by reference in its entirety.

DESCRIPTION

The invention relates to a piercing device for taking blood for medical analyses, comprising a base body, comprising at least one needle which is arranged therein and has a tip which can be extended, comprising a needle holding element which encloses the needle at least in part and a drive unit for driving a movement of the needle together with the needle holding element with respect to the base body.

Piercing devices of this type are known in various respects. For example, there are piercing devices which by means of a drive unit comprise a plunger-like element, having a spring connected thereto in a wide range of forms such as a spiral spring or a leg spring, and a needle holding element which is driven by this plunger. As a result, the needle or respectively lancet is slid forwards and exits the piercing device or respectively base body so as to pierce the skin of a patient.

If it is desired for the lancet or respectively needle to be retracted immediately after the piercing process and disappear into the base body or respectively housing of the piercing device, in piercing devices of this type there are a wide range of types of curved path which, as a result of the curved extension, initially make it possible for the needle holding element, which is equipped for example with a projection which extends within a curved path of this type, initially to exit the base body forwards and subsequently be retracted back into the body, since at this point the curved path is formed extending backwards or respectively rearwards again.

Piercing devices of this type generally have the drawback that they experience an additional movement of the needle or respectively needle element when the piercing device is biased again, after a piercing process has previously been carried out and before a further piercing process is triggered. The resulting movement of the lancet or respectively needle is generally undesired, since it requires high complexity of components operating inside one another, a large constructional space, high manufacturing costs and the movement of a large number of components during the tensioning process.

Accordingly, the object of the invention is to provide a piercing device for taking blood for medical analysis, comprising a base body, a needle, a needle holding element and a drive unit, in which a biasing process for a new piercing sequence or respectively piercing process can take place without simultaneous movement of the needle.

This object is achieved in accordance with the features of claim 1.

An essential aspect of the invention is that in a piercing device for taking blood for medical analyses, comprising a base body, comprising at least one needle which is arranged therein and has a tip which can be extended, comprising a needle holding element which encloses the needle at least in part and a drive unit for driving a movement of the needle together with the needle holding element with respect to the base body, a rotary element is arranged, which is provided between the drive unit and the needle holding element as a connection element for carrying out a rotary movement, and the rotary movement, both to the left and to the right, respectively brings about the movement of the needle holding element both forwards and backwards.

In other words, irrespective of whether the rotary element rotates to the left or rotates to the right, that is to say clockwise or anticlockwise, the arrangement of a rotary element of this type can bring about both a forward and a backward movement of the needle holding element during a rotary movement of this type in only one direction.

The drive element can be moved linearly and is equipped with at least two engagement arms, a respective one of the engagement arms engaging in one of at least two projections on the rotary element, and the other projection being deflectable by means of a curved path on the other engagement arm without taking on an engagement position with the other engagement arm, during each rotary movement. This makes it possible for either one engagement arm or the other engagement arm to engage in one of the projections, alternating as a function of the direction of rotation of the rotary movement, but without the further engagement arm engaging in the remaining projection at the same time. This makes it possible for the rotary element to rotate back and forth for the different piercing processes. In this context, it is important that the first projection and the first engagement arm, as seen in the piercing direction, are arranged to the left of a longitudinal axis which extends through an axis of rotation of the rotary element, and the second projection and second engagement arm are arranged to the right of the longitudinal axis. In this way, a rotary movement of the projection, which at this time is engaged in the engagement arm, from left to right or from right to left along the longitudinal axis, and thus also a forward and backward displacement of the needle holding element which is likewise connected to the rotary element, can always be brought about.

A kind of curved path is thus described by the rotary movement of the rotary element, and at the same time the arrangement of an engagement arm and the two projections on the rotary element ensures that the lancet or respectively needle moves back and forth both during a leftward and during a rightward rotary movement. This eliminates the need to move the lancet or respectively needle again when a biasing process takes place so as to bias the drive element again for a new piercing process.

The rotary element is advantageously in the form of a disc-like element, having an axis of rotation arranged perpendicular to the plane of the disc and to the direction of movement of the needle holding element, and the two projections are arranged at the edges of flexibly formed tongue-like elements of the disc plane, the tongue-like elements being deflected in the direction of the path of the axis of rotation. As a result, because of the deflection of one of the two tongue-like elements, the projection arranged thereon can be deflected with respect to the engagement arm associated therewith, whilst the other engagement arm engages in the projection and thus carries out the actual piercing process.

A first portion of the curved path is arranged below a first tongue-like element and a second portion is arranged below a second tongue-like element at an inclination to the disc-like element. A ramp-like formation of this type of the curve path provokes that one projection can be lowered, specifically by means of the inherent bias of the tongue-like element or by means of a pin-like element which is arranged below the tongue-like element and in a path which encloses the pin and which captures the ramp-like curved path in the extension thereof and engages around the pin and pulls it downwards.

The portions of the curved paths are preferably arc-shaped in form. Further, this preferably also applies to the tongue-like elements.

In accordance with a preferred embodiment, at least one connecting rod element is arranged which articulates the rotary element to the needle holding element, a projection on the first end of the connecting rod element engaging in a slot arranged on the rotary element and a projection on the second end of the connecting rod element engaging in a recess made complementary thereto on the needle holding element. This makes it possible for the rotary movement of the rotary element to be converted into a translational or respectively linear movement of the needle holding element, irrespective of whether the rotary element is rotating to the left or to the right.

The first end of the connecting rod element likewise engages in a further curved path, which is connected to the base body and the extension of which is equipped, in a V-shape and/or curved shape, with a centrally arranged maximum in the direction of the needle holding element. This ensures that the connecting rod element is likewise guided onto a predetermined path by the further curved path, this curved path already being ensured simply by the fastening of the connecting rod element to the rotary element. In this regard, a further curved path of this type serves as a counter bearing for the end of the connecting rod element.

Preferably, the drive unit can be spring-loaded using at least one spring element, this possibly being a spiral spring which acts in the piercing direction, is arranged inside the drive unit and can move a plunger-like element comprising engagement arms arranged thereon forwards or backwards.

During a rotary movement of the rotary element, in each case a projection can be moved, by the engagement arm engaging therein, from one side to the other side of the longitudinal axis on an arced path in one plane.

Further advantageous embodiments may be taken from the dependent claims.

Advantages and expedient aspects may be taken from the following description in connection with the drawings, in which.

Figure 1:
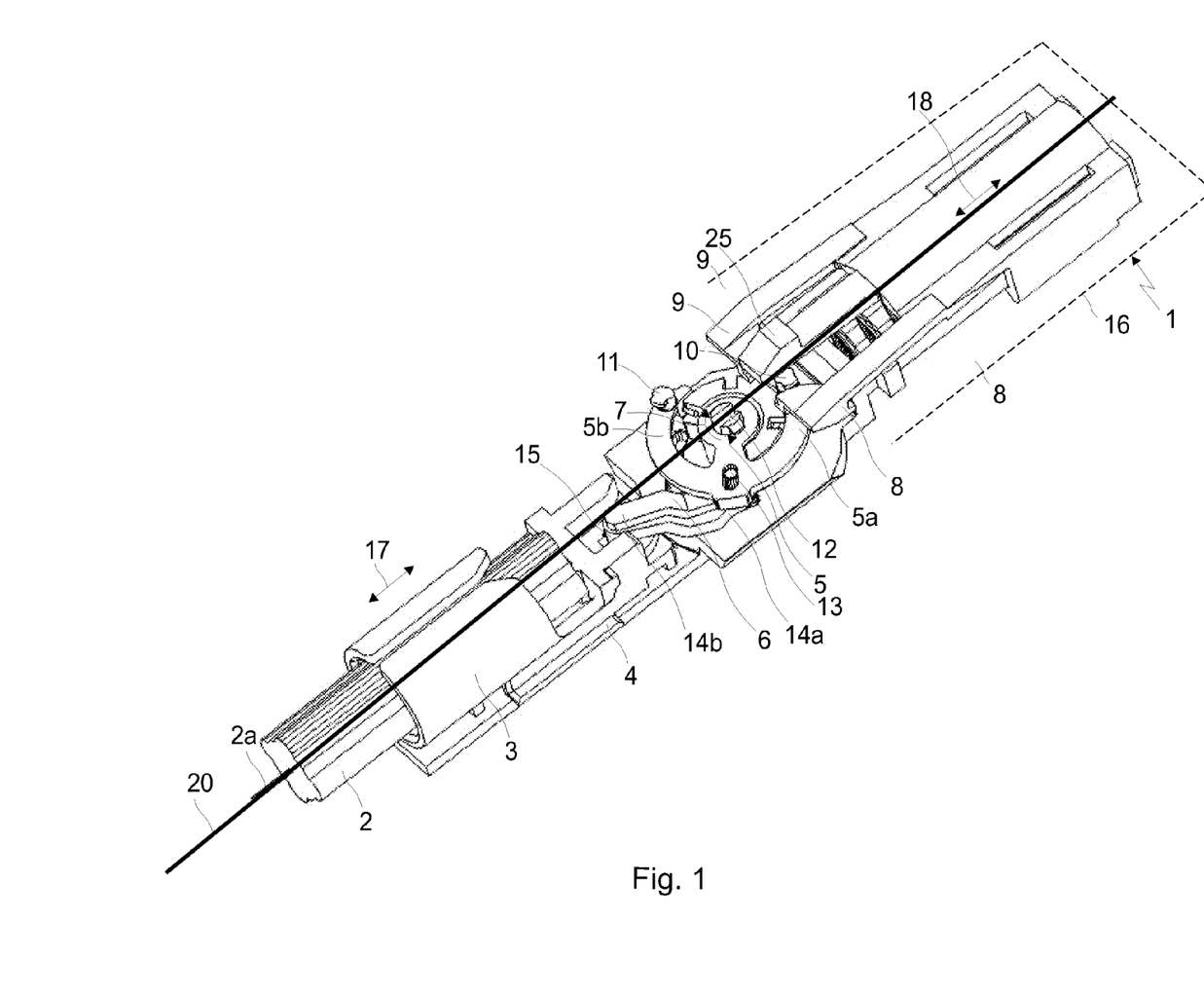
FIG. 1 is a perspective drawing of parts of a piercing device according to the invention.

FIG. 1 is a perspective drawing of the piercing device according to the invention in parts. The piercing device according to the invention basically consists of the following parts arranged in the interior of the housing 16, which is merely indicated here: a drive unit 1, a needle 2 comprising a needle holding element 3, a guide element 4 in which the needle holding element can be displaced linearly in a direction 17, a rotary element 5 and a connecting rod 6.

The drive unit 1 can be displaced forwards and backwards according to the double-headed arrow 18, in such a way that as a result the tip 2a of the needle 2 can be extended from a housing (not shown in greater detail here) and retracted again. This is shown by the double-headed arrow 17.

The rotary element 5, having an axis of rotation 12 which is positioned on a longitudinal axis 20, is arranged in the extension of the needle or respectively lancet 2. The rotary element 5 can be rotated about this axis 12 according to the double-headed arrow 7, the axis 12 being orientated perpendicular to the longitudinal axis 20 and perpendicular to the forward and backward movement 17 of the needle 2.

The rotary element 5 comprises two tongue-like elements 5a and 5b, which either deflect downwards automatically or can be bent under a prepared bias force, once there is no longer a counter element pressing against them from below, or are pushed downwards by means of slide paths or curved paths arranged below them via pins arranged on the tongue-like elements 5a and 5b, once there is no counter bearing or counter-loaded element acting on them from below.

The rotary element 5 is formed in the manner of a rotary disc and forms a connection between the drive unit 1, which can be moved forwards and backwards, and the connecting rod 6, which is in turn connected to the needle holding element 3.

The connecting rod 6 is connected to the rotary element 5 by means of a pin 13. This pin is arranged on a first end 14a of the connecting rod 6.

A pin 15 is also arranged on the second end 14b of the connecting rod 6, which is in turn connected to the needle holding element 3, in such a way that when the rotary element 5 is rotated the needle holding element 13 undergoes a forwards and backwards movement 17 as a result of sliding inside the guide element 4.

Two projections 10, 11, which are arranged on the upper face of the rotary element 5, can engage in two engagement arms 8, 9 of the drive unit 1, only one of these projections 10, 11 ever engaging in one of the engagement arms 8, 9 in each case.

A further engagement arm 25 serves to bias the drive unit 1 again after the piercing process is complete, by means of components (not shown here in greater detail) which are arranged on the housing 16 and may be connected to a manual actuation lever.

Figure 2:
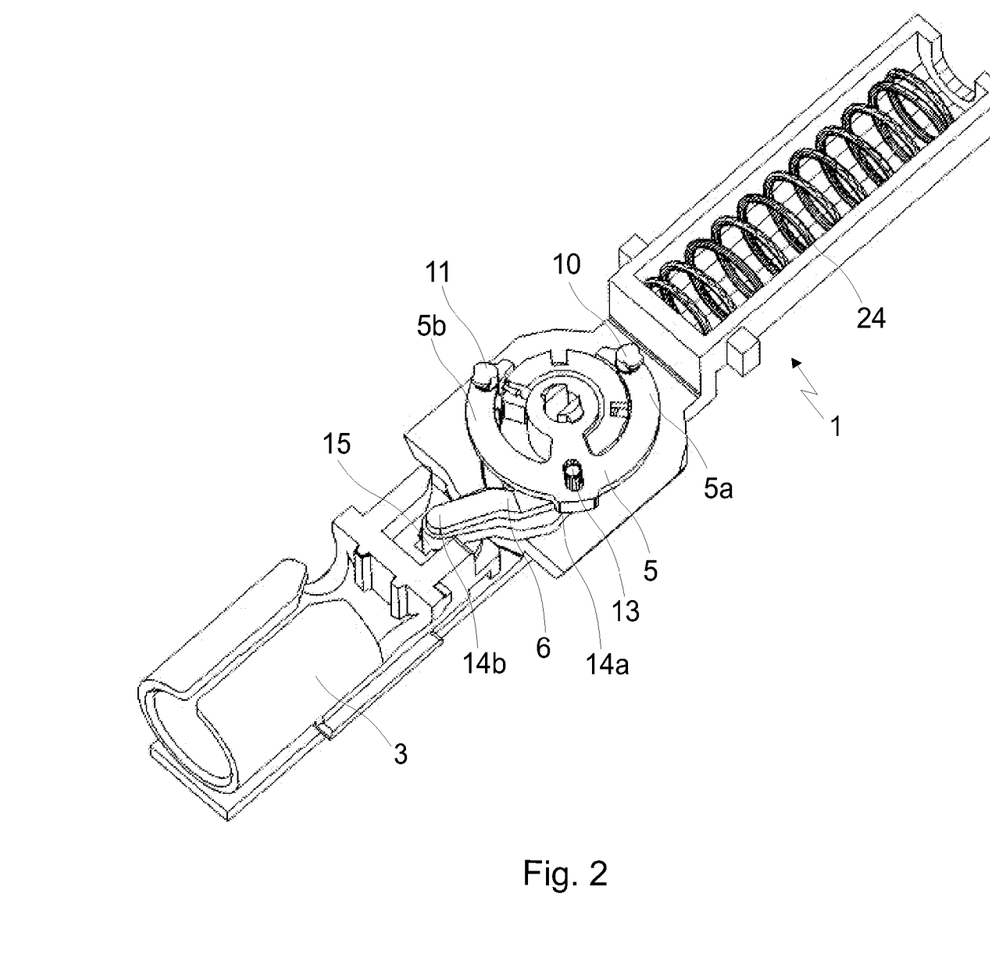
FIG. 2 is a perspective drawing of parts of the piercing device according to the invention with the spring element visible.

FIG. 2 and FIG. 3 again show the piercing device according to the invention as shown in FIG. 1, with further elements or in an exploded view.

FIG. 2 shows a spring element 24 inside the drive unit 1, which element is responsible for setting a bias so as subsequently to be able to carry out a piercing process. This spring element, in the form of a spiral spring which can act in the longitudinal direction along the longitudinal axis 20 of the piercing device, can be biased when extended and subsequently pulls the engagement arms 8, 9 backwards by means of components (not shown in greater detail) so as to set the rotary element 5 in rotation 7. In this drawing, the lancet or respectively needle 2 is not shown, simply the needle holding element 3 is shown instead.

Figure 3:
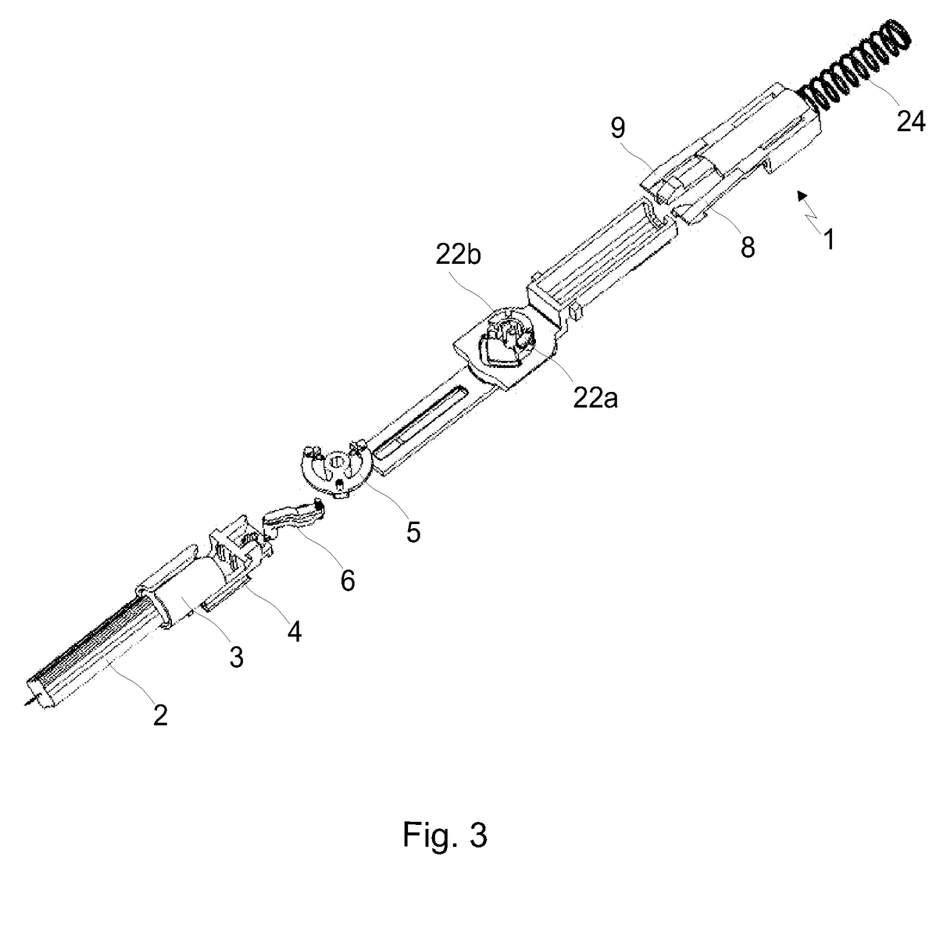
FIG. 3 is an exploded drawing of the parts of the piercing device according to the invention.

FIG. 3 is an exploded drawing, again showing the individual parts of the piercing device according to the invention as shown in FIG. 1 and FIG. 2. From this drawing, it can be seen that the piercing device according to the invention basically consists of the needle 2, the needle holding element 3, the guide element 4, the connecting rod 6, the rotary element 5, slide path portions 22a and 22b, the engagement arms 8, 9 together with the associated drive unit 1, and the spiral spring 24.

Figure 4:
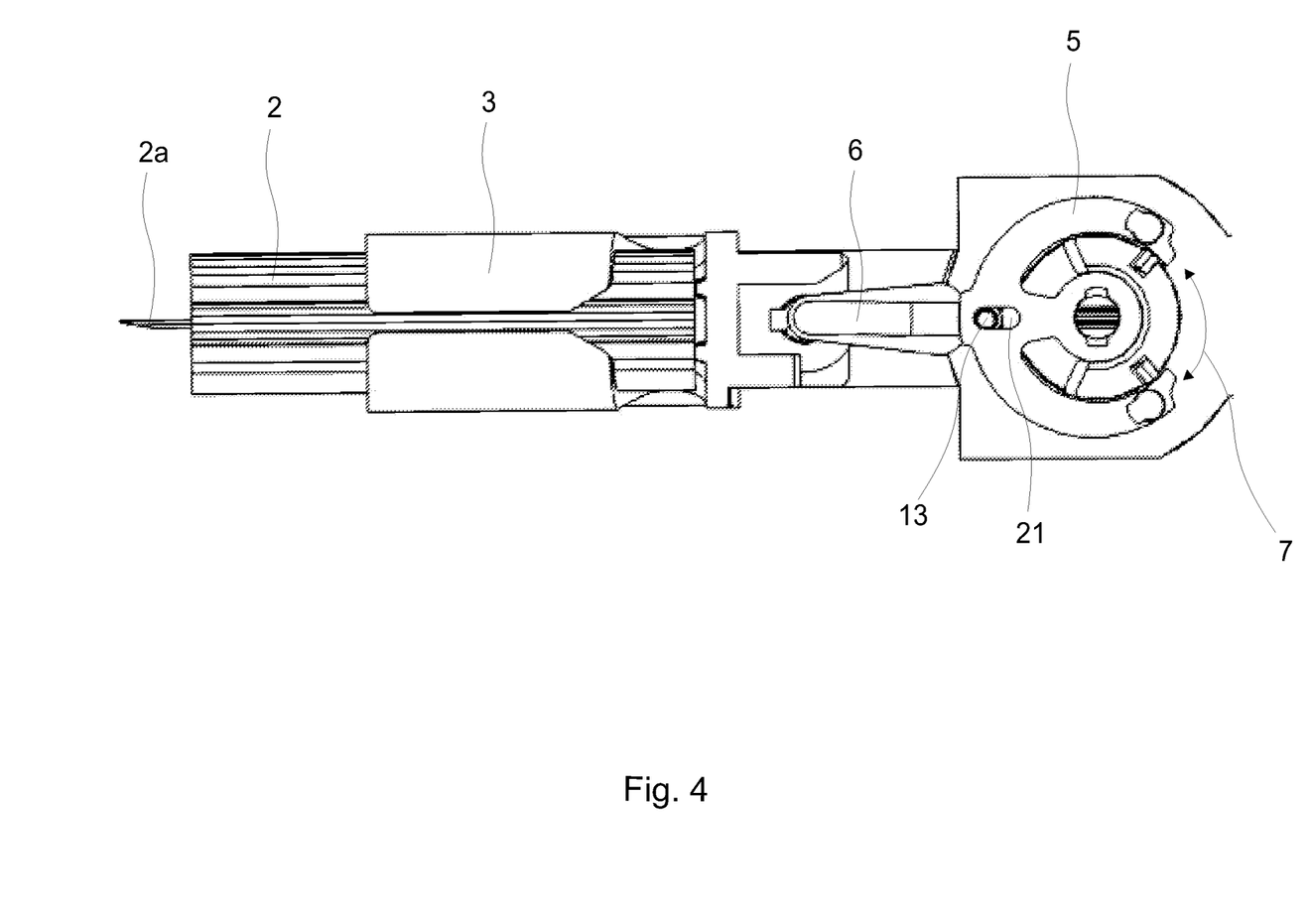
FIG. 4 is a detail of part of the piercing device shown in FIG. 1-3, in a plan view.

FIG. 4 is a plan view of a detail of the piercing device according to the invention as shown in FIG. 1-3. From this drawing, it can be seen that the rotary element 5 moves the connecting rod 6 inside a slot 21 via the pin 13 during a rotary movement 7. This makes the necessary play possible when converting the rotary movement 7 of the rotary element 5 into the pivot movement of the connecting rod 6 and during the subsequent linear movement of the needle holding element 3.

Figure 5:
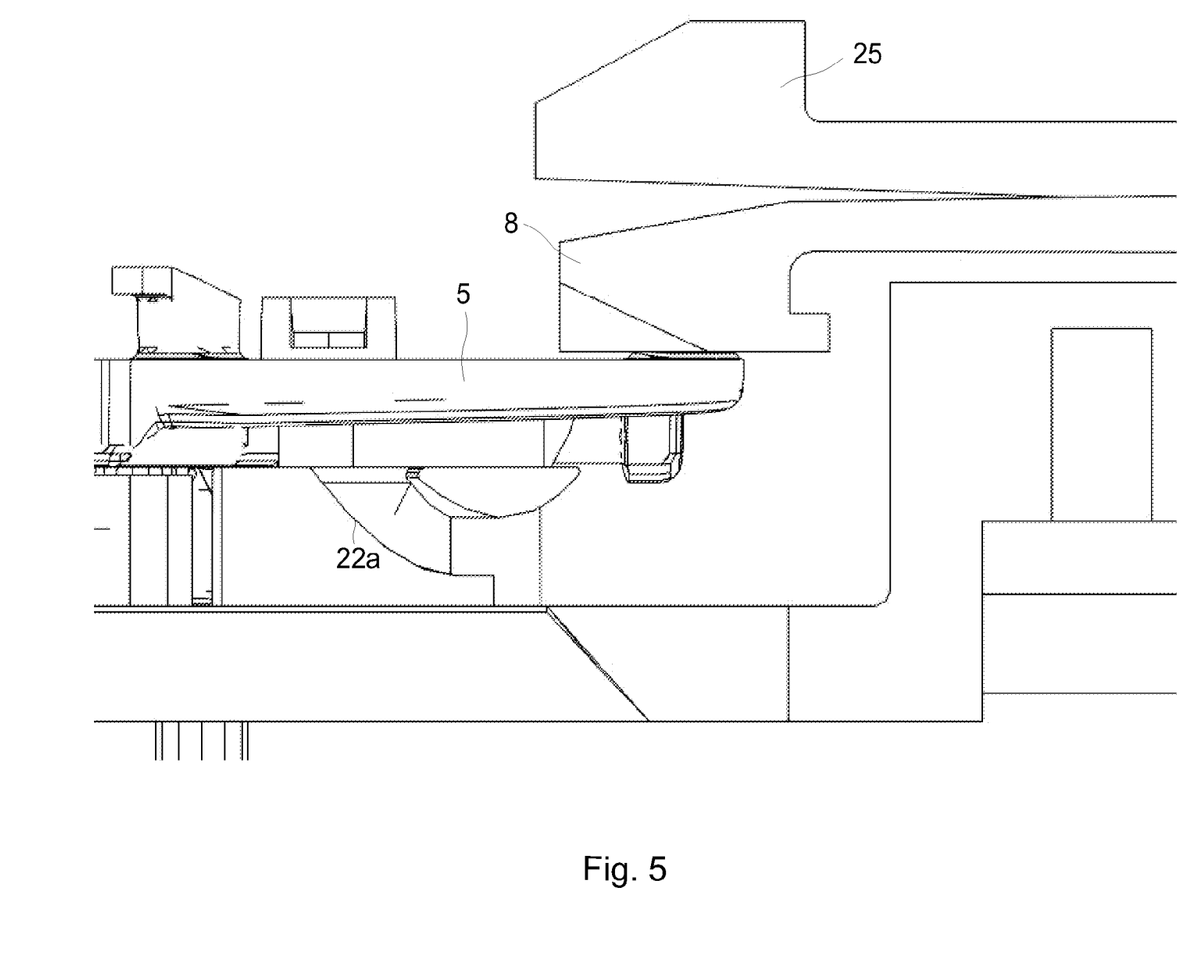
FIG. 5 is a side view of a detail of the parts shown in FIG. 1-3 of the piercing device according to the invention.

FIG. 5 is a side view of a detail comprising the rotary element 5 in accordance with the piercing device according to the invention. From this drawing, it can be seen that during rotation of the rotary element 5 the tongue-like element 5a arranged on this side can be pulled downwards along the portion 22a of the curved path, which is formed in the manner of a ramp, so as to make it possible for the projection 10 on the engagement arm 8 to slide past underneath, and thus not prevent an engagement position between the engagement arm 8 and the projection 10 from taking place, since at this time an engagement position between the engagement arm 9 and the projection 11 should take place.

Figure 6:
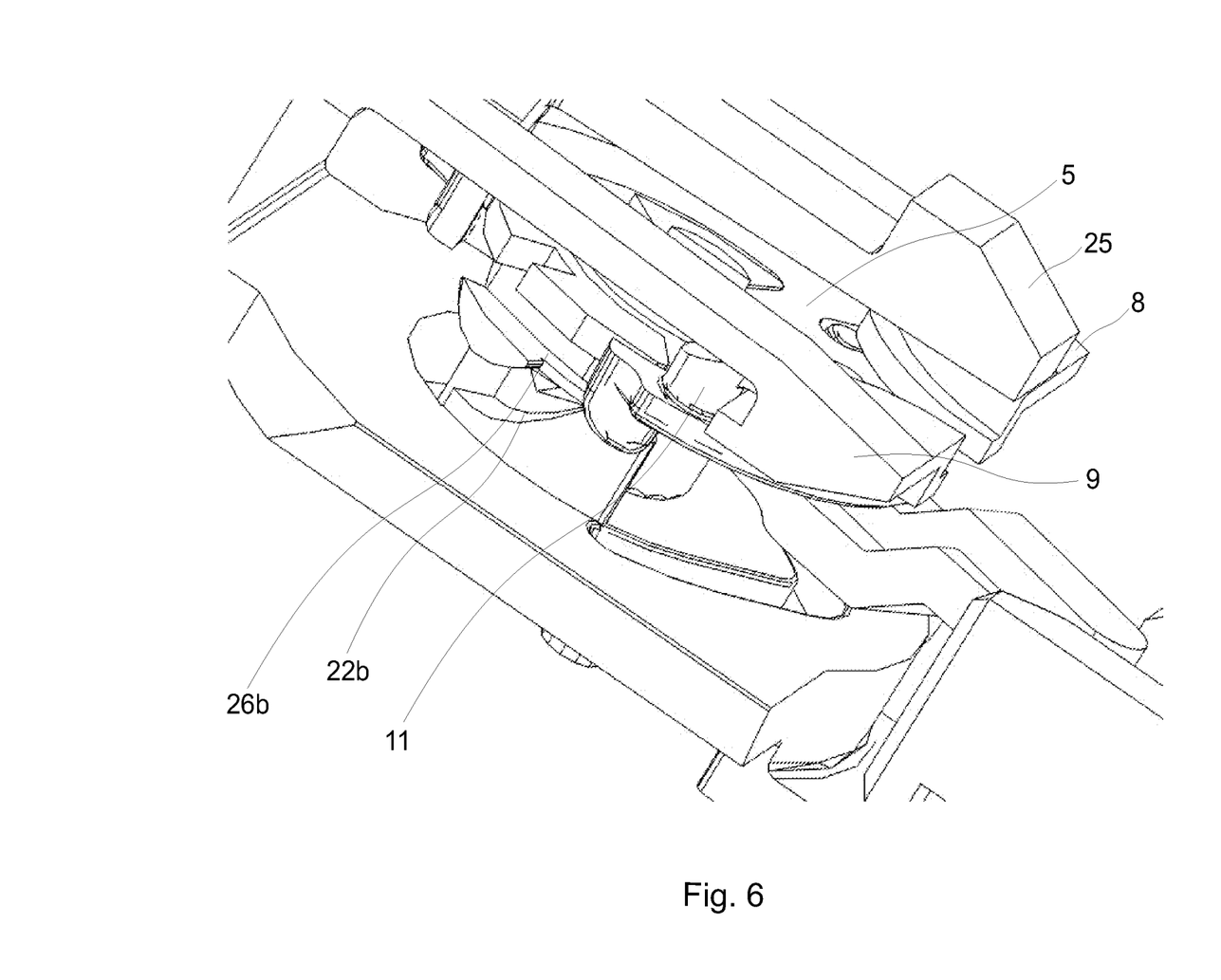
FIG. 6 is a perspective drawing of a detail of parts shown in FIG. 1-3 of the piercing device according to the invention.

FIG. 6 is a perspective drawing again showing the detail comprising the rotary element and the engagement arms in accordance with the piercing device according to the invention. It can clearly be seen from the drawing that a ramp-like portion 22b of the slide path or respectively curved path—along which the projection 11 can also slide under the engagement arm 9 when there is no engagement situation between the engagement arm 9 and the projection 11 and the engagement arm 9 thus fails to engage in the projection—is also arranged on the other side, that is to say on the side with the engagement arm 9.

However, in the drawing of FIG. 6, in the position of the rotary element 5 at this time there is an engagement between the projection 11 and the engagement arm 9, and the projection 11 can slide along a further portion 26b of the curved path in an engagement position above the portion 22b, and in doing so remains in position with respect to the engagement arm 9. In this way, one of the two projections 10, 11 can always be displaced downwards along the portion 22a or 22b, whilst the other of the two projections 10, 11 is pulled backwards by means of one of the two engagement arms 8 or 9 in an engagement position. As a result, the rotary element moves the pin 13 from a position—with respect to the longitudinal axis 20—in the left region into a position in the right region or vice versa.

If this is a rotary movement of the rotary element to the right, the projection 10 is pulled by the engagement arm 8. If it is a rotary movement to the left, the projection 11 is pulled from right to left and backwards by means of the engagement arm 9. In both cases, the needle 2 is in each case extended and retracted and the needle holding element 3 is displaced forwards and backwards, since the first end 14a of the connecting rod 6 passes a maximum, which is directed in the piercing direction, while the rotary movement is taking place. Advantageously, this results in retraction and extension of the needle holding element being achieved during the piercing process as a result of a single rotary movement.

Subsequently, retraction and extension for a further piercing process can in turn be carried out by way of a rotary movement in the opposite direction. However, between the two piercing processes, the spiral spring 25 can be biased by means of the engagement arm 25, without the rotary element and thus also the needle holding element 3b having to be moved as a result.

Figure 7:
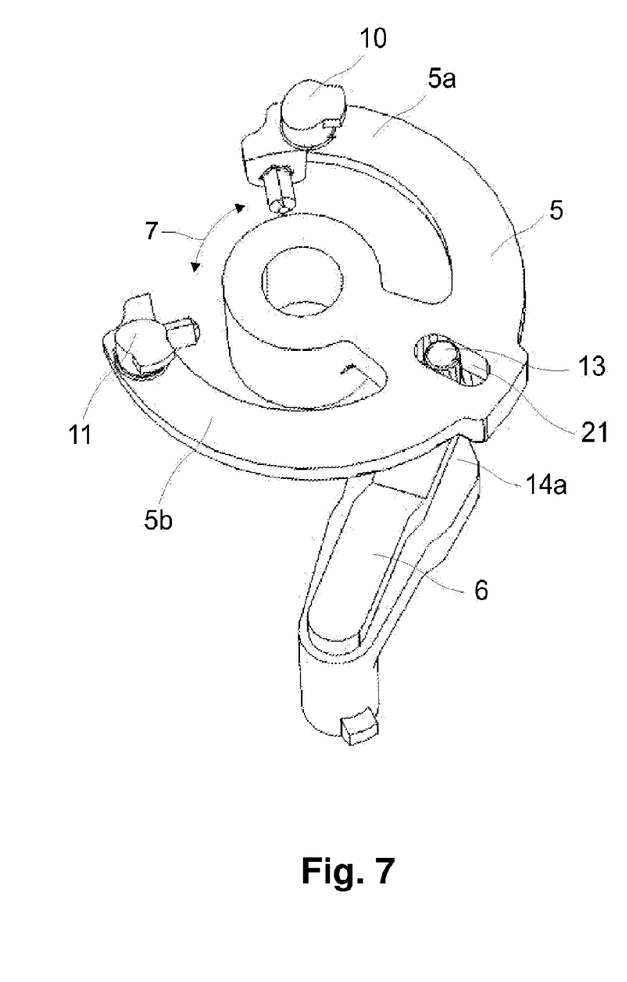
FIG. 7 is a perspective drawing of a rotary element of the piercing device according to the invention.

FIG. 7 is a perspective drawing again showing the rotary element 5 together with the two tongue-like elements 5a and 5b on which the projections 10, 11 are arranged. From this drawing, it can clearly be seen that the pin 13 of the first end 14a of the connecting rod 6 engages in a slot 21 which provides the necessary cooperation of the connecting rod and the rotary element 5.

The projections 10, 11 are formed in such a way that they advantageously have tongue-like projections at the position where the engagement arms 8, 9 can engage in the manner of clips.

Figure 8:
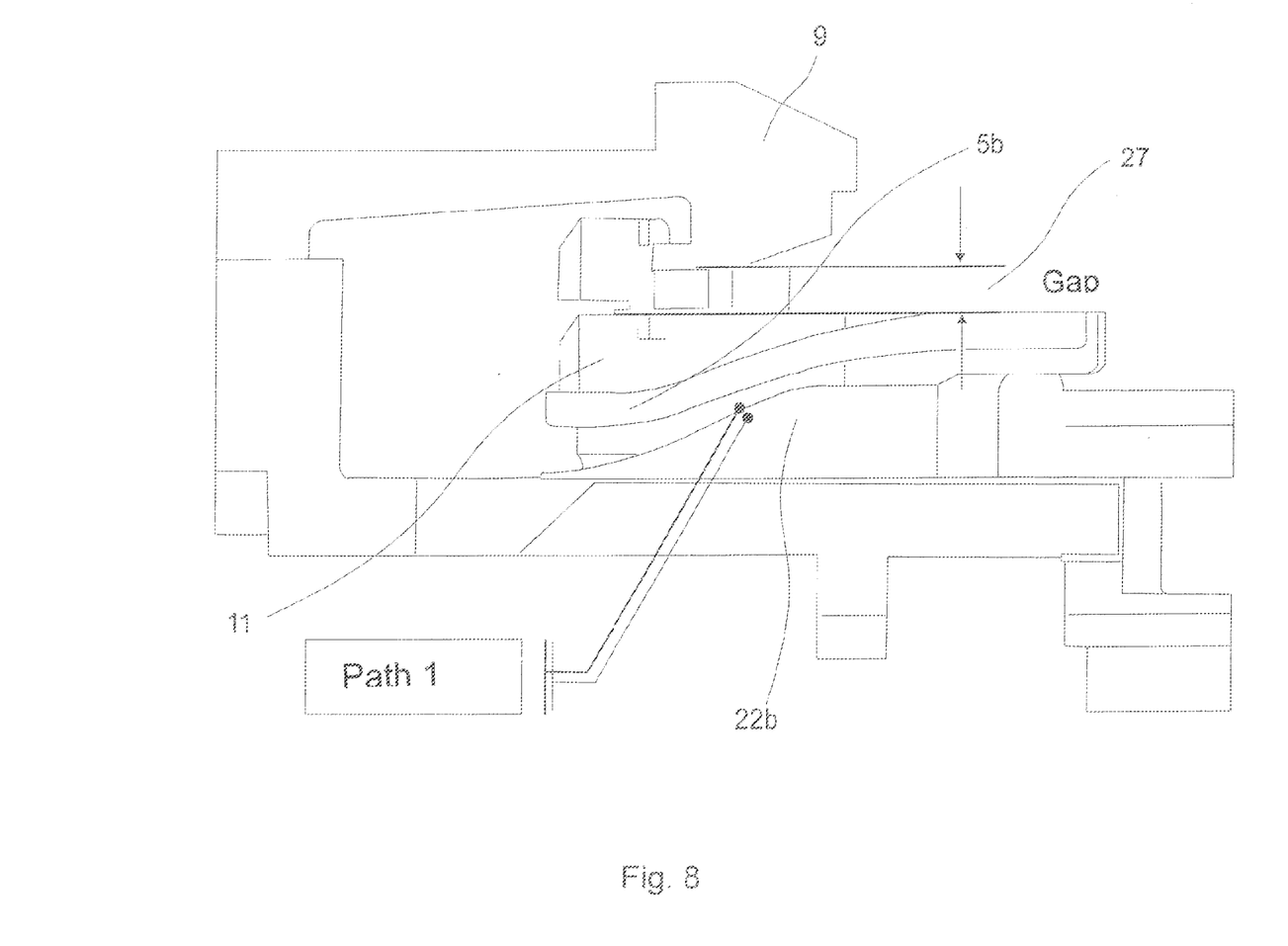
FIG. 8 is a side view of the rotary element having a curved path in accordance with a first embodiment of the invention.

FIG. 8 shows the rotary element together with the curved path in accordance with a first embodiment of the invention. In this drawing, it can be seen that the curved path 22b can be formed in the manner of a ramp and the projection 11 together with the tongue-like element 5b is immediately positioned in the lowered shape as a result of running along the ramp-like curve path 22b. In this position, the engagement arm 9 can slide away via the projection arm 11, without touching it. This is desired in this position, in which the engagement arm 8 is intended to engage in the projection 10 at this time. There is therefore a gap 27 between the engagement arm 9 and the projection 11.

Figure 9:
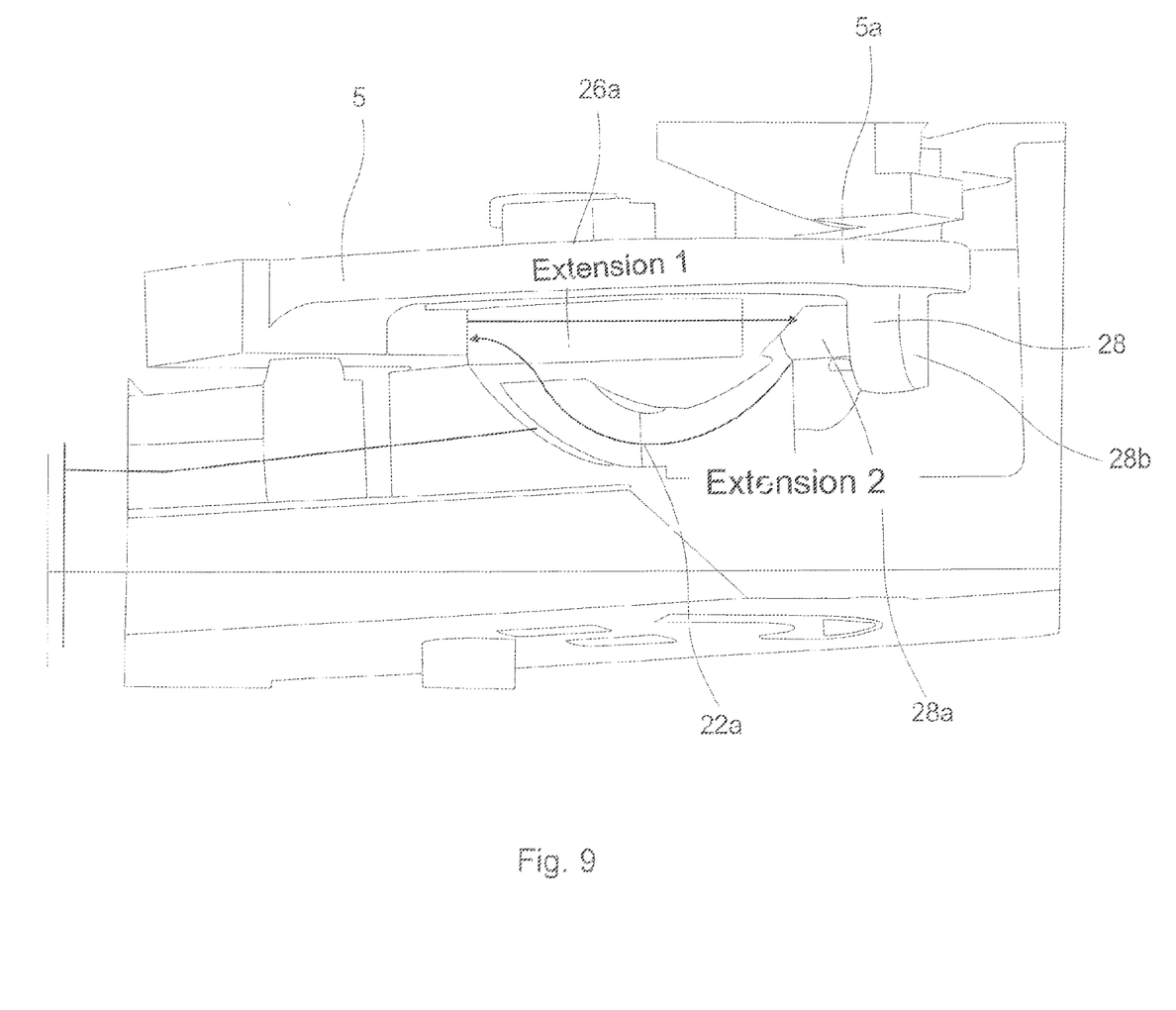
FIG. 9 shows the rotary element together with a piercing device according to the invention having a curved path in accordance with a second embodiment of the invention.

FIG. 9 is a detail of the rotary element together with a curved path in accordance with a second embodiment of the invention. From this drawing, it can be seen that the curved path has the first portion 22a and the second portion 26a. Thus, the tongue-like element 5a having the projection 28 arranged on the underside can pass through under the engagement arm when the rotary element moves to the left, as is shown by way of the curved path portion 22a. By contrast, if the rotary element 5 moves to the right, the projection 28 and thus the tongue-like element 5a travel on an upper curved path portion 26a, so as to remain in the engagement position with the engagement arm 8.

This functionality of the different paths during rotation to the right and to the left is ensured by forming a projection 28 which extends in the curved path portion 26a by means of a relatively small cylindrical element 28a and which extends in the lower curved path portion 22a by means of a relatively large cylinder-like portion 28b.

A formation of this type of the rotary element, which can be rotated to the left and to the right, and a cooperation with the engagement arms 8, 9, and in particular with the curved path portion 22a, 22b and if appropriate 26a and 26b, make it possible for the engagement arms 8, 9 to engage alternately in one of the recesses 10, 11 so as to move the needle forwards and backwards during a piercing process and make it possible to bias the drive unit manually after the piercing process is complete without the needle having to be moved for this purpose. Furthermore, the needle remains in the rest position of the biasing process, and subsequently the other projection having the other engagement arm can be used for carrying out the further piercing process.

Figure 10:
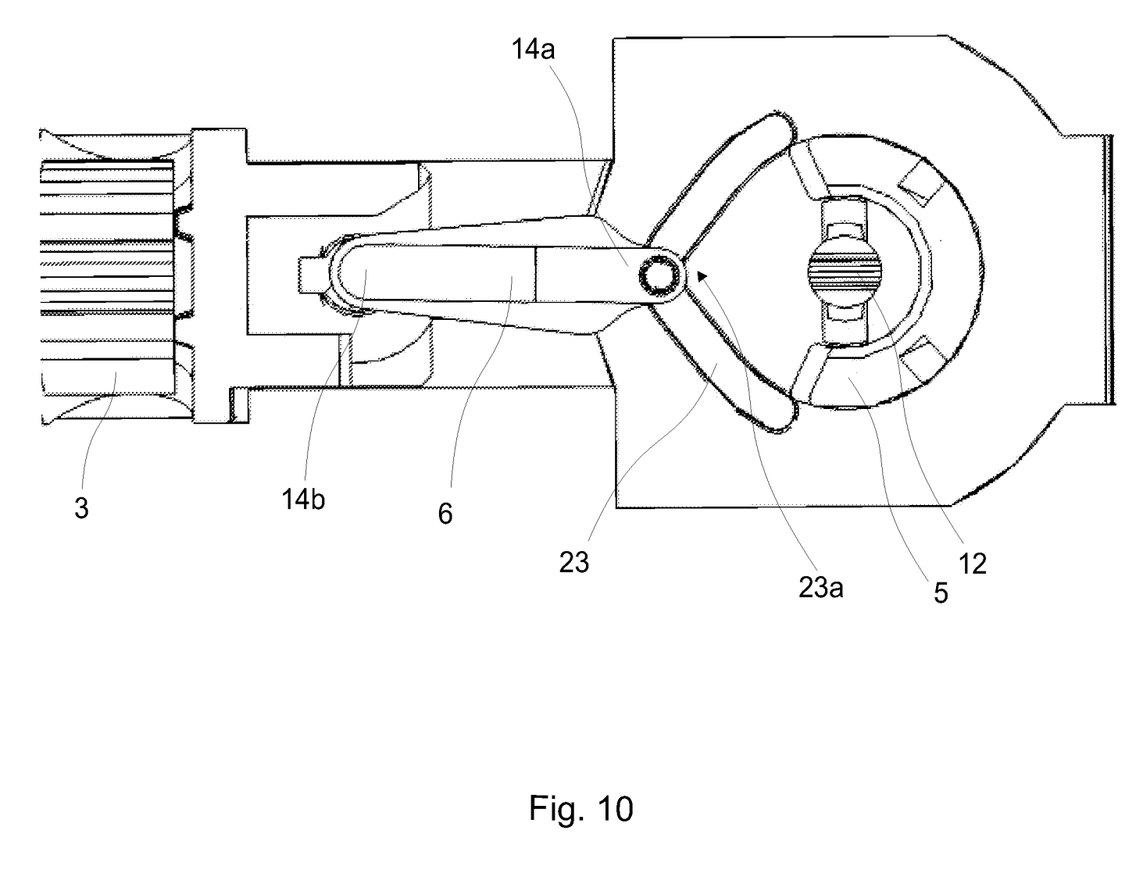
FIG. 10 is a plan view of the rotary element together with further components of the piercing device according to the invention.

FIG. 10 shows a further curved path 23 in which the connecting rod 6 also engages.

Certain features disclosed in the application are understood to be novel, including for example features either individually or in combination with other features as compared with the prior art.

LIST OF REFERENCE NUMERALS 1 drive unit
2 needle
2a tip
3 needle holding element 5 rotary element
5a first tongue-like element
5b second tongue-like element
6 connecting rod element
7 rotary movement
8 engagement arm
9 engagement arm
10 projection
11 projection
12 axis of rotation
13 projection
14a first end of the connecting rod element
14b second end of the connecting rod element
15 projection
16 base body
17 backward movement
18 linear movement
19 piercing direction
20 longitudinal axis
21 slot
22a first portion of the curved path
22b second portion of the curved path
23 further curved path
23a maximum
24 spiral spring
25 engagement arm
26a curved path portion
26b curved path portion
27 gap between engagement arm and projection
28 projection
28a cylindrical element

The invention claimed is:

1. A piercing device for taking blood for medical analyses, comprising a base body, comprising at least one needle which is arranged therein and a tip which can be extended, comprising a needle holding element which encloses the needle at least in part and comprising a drive unit for driving a movement of the needle together with the needle holding element with respect to the base body, wherein a rotary element for carrying out a rotary movement is arranged between the drive unit and the needle holding element as a connection element, and the rotary movement, both left and right, respectively brings about the movement of the needle holding element both forwards and backwards, wherein the drive unit can be moved linearly and has at least a first and a second engagement arm, a first one of which engages in a first one of at least a first and a second projection on the rotary element, the second projection being deflectable by means of a curved path on the second engagement arm without said second projection taking on an engagement position with the second engagement arm, during each rotary movement.

2. The piercing device according to claim 1, wherein the first projection and the first engagement arm, as seen in the piercing direction, are arranged left of a longitudinal axis which extends through an axis of rotation of the rotary element, and the second projection and second engagement arm are arranged right of the longitudinal axis.

3. The piercing device according to claim 2, wherein, during said rotary movement of the rotary element, each of the first and second projections can be moved, by the respective first and second engagement arms engaging therein, from one side to another side of the longitudinal axis on an arced path in one plane.

4. The piercing device according to claim 1, wherein the rotary element is in the form of a disc-shaped element, having an axis of rotation arranged perpendicular to the plane of the disc and to the direction of movement of the needle holding element, and the first and second projections are arranged at the edges of flexibly formed tongue-shaped elements of the disc plane, the tongue-shaped elements being deflected in a direction of the extension of the axis of rotation.

5. The piercing device according to claim 4, wherein a first portion of the curved path is arranged below a first tongue-shaped element and a second portion of the curved path is arranged below a second tongue-shaped element at an inclination towards the disc-shaped element.

6. The piercing device according to claim 5, wherein the first and second portions of the curved path are arc-shaped in form.

7. The piercing device according to claim 1, comprising at least one connecting rod element which articulates the rotary element to the needle holding element, a projection on a first end of the connecting rod element engaging in a slot arranged on the rotary element and a projection on a second end of the connecting rod element engaging in a recess made complementary thereto on the needle holding element.

8. The piercing device according to claim 7, wherein the first end of the connecting rod element also engages in a further curved path, which is connected to the base body and an extension of which is equipped, in a V-shape and/or curved shape, with a centrally arranged maximum in a direction of the needle holding element.

9. The piercing device according to claim 1, wherein the drive unit is spring-loaded using at least one spring element.

10. The piercing device according to claim 9, wherein the drive unit is spring-loaded using at least one spiral spring which acts in the piercing direction.

11. The piercing device according to claim 1, wherein a first engagement arm engages a first projection on the rotary element, and wherein a second projection is deflectable by means of said curved path on the second engagement arm without said second projection taking on an engagement position with the second engagement arm, during each rotary movement.

\* \* \* \* \*